United States Patent

Tan et al.

[11] Patent Number: 5,866,242
[45] Date of Patent: Feb. 2, 1999

[54] SOFT, STRONG, ABSORBENT MATERIAL FOR USE IN ABSORBENT ARTICLES

[75] Inventors: Erol Tan; Peter R. Abitz, both of St. Simons Island, Ga.

[73] Assignee: Rayonier Inc., Stamford, Conn.

[21] Appl. No.: 784,536

[22] Filed: Jan. 17, 1997

[51] Int. Cl.$^6$ ...................................................... B32B 7/02
[52] U.S. Cl. .......................... 428/219; 442/381; 442/385; 442/393; 442/417
[58] Field of Search .................................. 442/381, 385, 442/393, 417; 428/219; 162/164.1, 157.2

[56] References Cited

U.S. PATENT DOCUMENTS

| | | |
|---|---|---|
| 4,610,678 | 9/1986 | Weisman et al. . |
| 5,516,569 | 5/1996 | Veith et al. . |
| 5,547,541 | 8/1996 | Hansen et al. . |
| 5,562,645 | 10/1996 | Tanzer et al. . |
| 5,635,239 | 6/1997 | Chen et al. . |
| 5,693,162 | 12/1997 | Gustafson et al. . |

FOREIGN PATENT DOCUMENTS 0763 364 A2   9/1996   European Pat. Off. .

*Primary Examiner*—Christopher Raimund
*Attorney, Agent, or Firm*—Rockey, Milnamow & Katz, Ltd.

[57] ABSTRACT

An absorbent material that can be used as an absorbent core in absorbent articles such as disposable diapers, feminine hygiene products and incontinence devices is provided. An absorbent material of this invention contains a blend of cellulosic fibers and a superabsorbent material. The absorbent material has superior wicking, strength and softness properties when compared to existing core materials. The material can be air-laid as a homogeneous blend of fiber and superabsorbent in one or more layers.

50 Claims, 4 Drawing Sheets

Feminine Hygiene Products:

Total Basis Weight ≅ 200 g/cm$^2$

Three Strata

10% SAP

Four Strata

20% or 40% SAP

Feminine Hygiene Products:

Total Basis Weight ≅ 200 g/cm$^2$

Three Strata

- 25 g/m$^2$ Pulp
- 150 g/m$^2$ (SAP + Pulp)
- 25 g/m$^2$ Pulp

10% SAP

Four Strata

- 25 g/m$^2$ Pulp
- 75 g/m$^2$ (Pulp + SAP)
- 75 g/m$^2$ (Pulp + SAP)
- 25 g/m$^2$ Pulp

20% or 40% SAP

FIG. 3

Diapers and Incontinence Products:

Total Weight ≅ 400 g/cm$^2$

Three Strata

- 50 g/m$^2$ Pulp
- 300 g/m$^2$ (SAP + Pulp)
- 50 g/m$^2$ Pulp

10% SAP

Four Strata

- 50 g/m$^2$ Pulp
- 150 g/m$^2$ (Pulp + SAP)
- 7150 g/m$^2$ (Pulp + SAP)
- 50 g/m$^2$ Pulp 20% or 40% SAP

SOFT, STRONG, ABSORBENT MATERIAL FOR USE IN ABSORBENT ARTICLES

TECHNICAL FIELD OF THE INVENTION

This invention relates to absorbent materials to be used as absorbent cores in articles such as disposable diapers, feminine hygiene products and incontinence devices. More particularly, the present invention relates to absorbent materials that are high density, strong, soft materials with superior wicking properties.

BACKGROUND OF THE INVENTION

Disposable absorbent articles, such as diapers, feminine hygiene products, adult incontinence devices and the like have found widespread acceptance. To function efficiently, such absorbent articles must quickly absorb body liquids, distribute those liquids within and throughout the absorbent article and be capable of retaining those body liquids when placed under loads. In addition, the absorbent article need be sufficiently soft and flexible so as to comfortably conform to body surfaces.

While the design of individual absorbent articles varies depending upon use, there are certain elements or components common to such articles. The absorbent article contains a liquid pervious top sheet or facing layer, which facing layer is designed to be in contact with a body surface. The facing layer is made of a material that allows for the unimpeded transfer of fluid from the body into the core of the article. The facing layer should not absorb fluid per se and, thus, should remain dry. The article further contains a liquid impervious back sheet or backing layer disposed on the outer surface of the article and which layer is designed to prevent the leakage of fluid out of the article.

Disposed between the facing layer and backing layer is an absorbent member referred to in the art as an absorbent core. The function of the absorbent core is to absorb and retain body fluids entering the absorbent article through the facing layer. Because the origin of body fluids is localized, it is necessary to provide a means for distributing fluid throughout the dimensions of the absorbent core. This is typically accomplished either by providing a distribution member disposed between the facing layer and absorbent core and/or altering the composition of the absorbent core per se.

Fluid can be distributed to different portions of the absorbent core by means of a transfer or acquisition layer disposed between the facing layer and core. Because of the proximity of such an acquisition layer to the body surface of the wearer, the acquisition layer should not be formed from material that retains large amounts of fluid. The purpose of the acquisition layer is to provide for rapid transfer and distribution of fluid to the absorbent core.

The absorbent core is typically formulated of a cellulosic wood fiber matrix or pulp, which pulp is capable of absorbing large quantities of fluid. Absorbent cores can be designed in a variety of ways to enhance fluid absorption and retention properties. By way of example, the fluid retention characteristics of absorbent cores can be greatly enhanced by disposing superabsorbent materials in amongst fibers of the wood pulp. Superabsorbent materials are well known in the art as substantially water-insoluble, absorbent polymeric compositions that are capable of absorbing large amounts of fluid in relation to their weight and forming hydrogels upon such absorption. Absorbent articles containing blends or mixtures of pulp and superabsorbents are known in the art.

The distribution of superbasorbents within an absorbent core can be uniform or non-uniform. By way of example, that portion of an absorbent core proximate to the backing layer (farthest away from the wearer) can be formulated to contain higher levels of superabsorbent than those portions of the core proximate the facing or acquisition layer. By way of further example, that portion of the core closest to the site of fluid entry (e.g., acquisition zone) can be formulated to wick fluid into surrounding portions of the core (e.g., storage zone).

In addition to blending pulp with superabsorbent material, a variety of other means for improving the characteristics of pulp have been described. For example, pulp boards can be more easily defiberized by using chemical debonding agents (see, e.g., U.S. Pat. No. 3,930,933). In addition, cellulose fibers of wood pulp can be flash-dried prior to incorporation into a composite web absorbent material (see, e.g., U.K. Patent Application GB 2272916A published on Jun. 1, 1994). Still further, the individualized cellulosic fibers of wood pulp can be cross-linked (see, e.g., U.S. Pat. Nos. 4,822,453; 4,888,093; 5,190,563; and 5,252,275). All of these expedients have the disadvantage of requiring the wood pulp manufacturer to perform time-intensive, expensive procedures during the wood pulp preparation steps. Thus, use of these steps results in substantial increases in the cost of wood pulp.

Although all of the above treatment steps have been reported to improve the absorption characteristics of pulp for use as absorbent cores, there are certain disadvantages associated with such treatments. By way of example, the manufacturer of the end use absorbent article (e.g. feminine hygiene product or diaper) must fluff the fibers in the wood pulp so as to detach the individual fibers bound in that pulp. Typically, pulp has a low moisture content which results in the individual fibers being relatively brittle. If the pulp manufacturer performs such fluffing prior to shipment to the absorbent article maker, the transportation costs of the pulp are increased. At least one pulp manufacturer has attempted to solve this problem by producing flash-dried pulp without chemical bonding agents in a narrow range of basis weights in pulp density (see U.S. Pat. No. 5,262,005). However, even with this process, the manufacturer of the absorbent article must still defiber the pulp after purchase.

There continues to be a need in the art, therefore, for a material that satisfies the absorbency requirements needed for use as absorbent core in disposable absorbent articles and which simultaneously provides time and cost savings to both the pulp manufacturer and the manufacturer of the absorbent article.

BRIEF SUMMARY OF THE INVENTION

In one aspect, the present invention provides an absorbent material having a basis weight of from about 200 $g/m^2$ to about 400 $g/m^2$, a density of from about 0.35 g/cc to about 0.40 g/cc and a ratio of Gurley stiffness (mg) to density (g/cc) of less than about 3700, wherein the material is air-laid as a bottom layer of pulp, a middle layer of pulp and superabsorbent polymer disposed in amongst the pulp, and a top layer of pulp. Preferably, the material comprises from about 10 weight percent to about 40 weight percent superabsorbent polymer. In one embodiment, the material has a basis weight of about 200 $g/m^2$ and comprises about 10 weight percent superabsorbent polymer. In another embodiment, the material has a basis weight of about 400 $g/m^2$ and comprises about 10 weight percent superabsorbent polymer.

The middle layer of a material of the present invention can comprise a first middle layer adjacent the bottom layer and a second middle layer adjacent the top layer. In accordance with this embodiment, the material has a basis weight of about 200 g/m² and comprises from about 20 weight percent to about 40 weight percent superabsorbent polymer or has a basis weight of about 400 g/m² and comprises from about 20 weight percent to about 40 weight percent superabsorbent polymer.

In preferred embodiments, the material has a ratio of Gurley stiffness to density of less than about 3250 or 3000. Preferably, the material has a ratio of pad integrity to density of greater than about 25.0, more preferably greater than about 30.0 and, most preferably, greater than about 35.0.

In another aspect, the present invention provides an absorbent material that comprises: (a) from about 40 weight percent to about 90 weight percent cellulosic fibers; and (b) from about 10 weight percent to about 60 weight percent superabsorbent polymer, the material having a water content of less than about 10 weight percent, a density of greater than about 0.25 g/cc and a ratio of Gurley stiffness (mg) to density (g/cc) of less than about 3700.

In accordance with this aspect, the material preferably contains from about 50 to about 90 weight percent cellulosic fibers and, more preferably from about 60 to about 80 weight percent cellulosic fibers. Such a material preferably contains from about 10 to about 50 weight percent superabsorbent polymer and, more preferably from about 20 to about 40 weight percent superabsorbent polymer.

Preferred densities of such material range from about 0.30 to about 0.55 g/cc, preferably from about 0.30 to about 0.45 g/cc and, more preferably from about 0.30 to about 0.40 g/cc. In other embodiments, the ratio of Gurley stiffness to density is less than about 3250 and, preferably less than about 3000.

In another embodiment, a material has a ratio of pad integrity to density of greater than about 25.0, preferably greater than about 30.0 and, more preferably greater than about 35.0. The material of this invention can have a basis weight of from about 50 g/m² to about 700 g/m². Preferably, that basis weight is from about 100 g/m² to about 600 g/m² and, more preferably from about 200 g/m² to about 400 g/m².

A material of the present invention can be air-laid as one or more layers. Preferably, the material is air-laid as 2, 3, 4 or 5 layers. At least one of the layers can contain cellulosic fibers to the exclusion of superabsorbent polymer.

In another embodiment, a material of the present invention has a 45° wicking distribution at 5 inches of at least 5 grams of saline per gram of material. Preferably, the 45° wicking distribution at 5 inches is at least 9 grams of saline per gram of material and, more preferably at least 11 grams of saline per gram of material.

The material of the present invention is thin having a thickness of from about 0.5 mm to about 2.5 mm. In preferred embodiments, the thickness is from about 1.0 mm to about 2.0 mm and, preferably from about 1.25 mm to about 1.75 mm. The material can further comprise from about 1 weight percent to about 20 weight percent synthetic fibers.

The material of this invention has superior superabsorbent polymer retaining characteristics. The material retains more than about 85 weight percent, preferably more than about 90 weight percent and, most preferably greater than about 95 weight percent of superabsorbent polymer after shaking for 10 minutes in a Ro-Tap Sieve Shaker.

A cellulosic fiber used in a material of the present invention preferably contains wood pulp. In a preferred embodiment, at least a portion of that pulp is produced by a process that includes the step of treating a liquid suspension of pulp at a temperature of from 15° C. to about 60° C. with an aqueous alkali metal salt solution having an alkali metal salt concentration of from about 2 weight percent to about 25 weight percent of said solution for a period of time ranging from about 5 minutes to about 60 minutes.

BRIEF DESCRIPTION OF THE DRAWINGS

In the drawings, which form a portion of the specification.

DETAILED DESCRIPTION OF THE INVENTION

The present invention provides novel, absorbent material that is particularly well suited for use as cores in absorbent articles such as diapers, feminine hygiene products, incontinence devices and the like. The material of the present invention is a blend or mixture of cellulosic fibers and superabsorbent disposed in and amongst fibers of that pulp. A material of this invention has a unique combination of softness, wicking and absorbency characteristics that make it particularly suitable for use in absorbent articles. An absorbent material of the present invention can be used directly by a manufacturer of the absorbent article without the need for any additional processing by that manufacturer other than cutting to the desired size and shape for the absorbent article.

The present invention relates to an absorbent material containing cellulosic fibers and superabsorbent polymers (SAP), which material is soft, thin, and of high density. Additionally, the material has enhanced absorption properties (rate and wicking) and firmly entraps SAP polymer in the fiber network without the use of any chemicals or binder. The absorbent has enough integrity (strength) to be processed on conventional disposable product manufacturing equipment without fiber breakage.

In one aspect, the present invention provides an absorbent material that contains from about 40 weight percent to about 90 weight percent cellulosic fibers; and from about 10 weight percent to about 60 weight percent SAP. The material has a water content of less than about 10 weight percent. As used herein, the phrase "weight percent" means weight of substance per weight of final material. By way of example, 10 weight percent SAP means 10 g/m² SAP per 100 g/m² basis weight of the material.

Cellulosic fibers that can be used in a material of the present invention are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

An absorbent material of the present invention can contain any SAP, which SAPs are well known in the art. As used herein, the term "SAP" means a substantially water-insoluble polymeric material capable of absorbing large quantities of fluid in relation to their weight. The SAP can be in the form of particulate matter, flakes, fibers and the like. Exemplary particulate forms include granules, pulverized particles, spheres, aggregates and agglomerates. Exemplary and preferred SAPs include salts of crosslinked polyacrylic acid such as sodium polyacrylate. SAPs are commercially available (e.g., Stockhausen GmbH, Krefeld, Germany).

In accordance with a preferred embodiment, the material contains from about 50 to about 90 weight percent cellulosic fibers and, more preferably from about 60 to about 80 weight percent cellulosic fibers. Such a material preferably contains from about 10 to about 50 weight percent SAP and, more preferably from about 20 to about 40 weight percent SAP.

Figure 1:
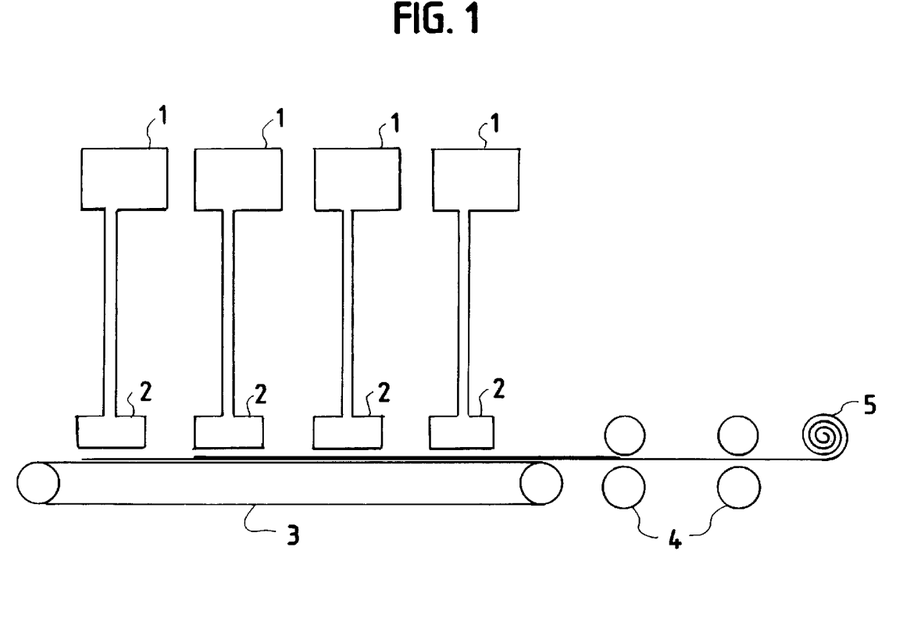
FIG. 1 is a schematic illustration of means for air-laying absorbent material of the present invention using four air-laying heads followed by means for compacting the air-laid material.

An absorbent material is made using air-laying means well known in the art (See FIG. 1). In accordance with FIG. 1, cellulosic fibers (e.g., pulp) are processed using a hammer mill to individualize the fibers. The individualized fibers are blended with SAP granules in a blending system 1 and pneumatically conveyed into a series of forming heads 2. The blending and distribution of absorbent materials can be controlled separately for each forming head. Controlled air circulation and winged agitators in each chamber produce uniform mixture and distribution of pulp and SAP. The SAP can be thoroughly and homogeneously blended throughout the web or contained only in specific strata by distributing it to selected forming heads. Fibers (and SAP) from each forming chamber are deposited by vacuum onto a forming wire 3 thus forming a layered absorbent web. The web is subsequently compressed using calenders 4 to achieve desirable density. The densified web is wound into a roll 5 using conventional winding equipment. The forming wire 3 can be covered with tissue paper to reduce the loss of material. The tissue paper layer can be removed prior to calendering or incorporated into the formed material.

An absorbent material of the present invention is of high density and has a density of greater than about 0.25 g/cc. In preferred embodiments, the material has density in the range of from about 0.30 g/cc to about 0.50 g/cc. More preferably, the density is from about 0.30 g/cc to about 0.45 g/cc and, even more preferably from about 0.35 g/cc to about 0.40 g/cc.

Air-laid absorbents are typically produced with a low density. To achieve higher density levels, such as preferred in the material of the present invention, the air-laid material is compacted using calenders as shown in FIG. 1. Compaction is accomplished using means well known in the art. Typically such compaction is carried out at a temperature of about 100° C. and a load of about 130 Newtons per millimeter. The upper compaction roll is typically made of steel while the lower compaction roll is a flexroll having a hardness of about 85 SH D. It is preferred that both the upper and lower compaction rolls be smooth, although the upper roll can be engraved. As set forth hereinafter in the Examples, use of an engraved upper roll may result in formation of a material having slower fluid absorption rates.

A high density absorbent material of the present invention is surprisingly and unexpectedly soft. The present material has a ratio of Gurley stiffness, measured in milligrams (mg) to density, measured in grams per cubic centimeter (g/cc) of less than about 3700. In preferred embodiments, that ratio of Gurley stiffness to density is less than about 3200 and, more preferably, less than about 3000.

Gurley stiffness is one of many indices of softness. Gurley stiffness measures the bendability or flexibility of absorbent materials. The lower the Gurley stiffness value, the more flexible the material. A material for use in absorbent materials such as diapers, sanitary napkins and the like has to be flexible so that is can comfortably conform to various body profiles. Increased flexibility is preferred. As set forth hereinafter in Example 1, Gurley stiffness was determined on absorbent material of the present invention as well as absorbent core material from two commercially available disposable diapers. The Gurley stiffness of all materials was determined at a number of different densities. The material of the present invention was substantially and significantly softer than existing, commercially available material at every density tested.

An absorbent material of the present invention is strong in light of its softness. Pad integrity is a well known measurement of absorbent material strength. A material of the present invention demonstrates strength (high pad integrity) over a wide range of densities (See the Examples hereinafter). A present material has a pad integrity, measured in Newtons (N), to density (g/cc) ratio of greater than about 25.0. In a preferred embodiment, that ratio is greater than about 30.0 and, even more preferably, greater than about 35.0. In contrast, the value of that ratio to commercially available absorbent core materials is substantially and significantly lower (e.g., less than about 24.0).

An absorbent material of this invention can be prepared over a wide range of basis weights without adversely affecting its softness or strength. Thus, the material can have a basis weight in the range of from about 50 g/m$^2$ to about 700 g/m$^2$. In a preferred embodiment, the basis weight ranges from about 100 g/m$^2$ to about 600 g/m$^2$ and, more preferably from about 200 g/m$^2$ to about 400 g/m$^2$.

An absorbent material of the present invention has enhanced wicking properties. Wicking is the ability of an absorbent material to direct fluid away from the point of fluid entry and distribute that fluid throughout the material. An absorbent material of this invention has surprisingly superior wicking properties when compared to absorbent cores from commercially available absorbent articles (e.g., Huggies® diapers). As described in detail hereinafter in the Examples, the wicking properties of two embodiments of a present invention wicked substantial amounts of fluid over 5 inches from the point of fluid entry. In a 400 g/m$^2$ basis weight, 20 weight percent SAP material, the 45° wicking distribution at 5 inches was about 12.2 grams of fluid per gram of material. That same material had a wicking distribution at 6 inches of about 7.7 grams of fluid and a distribution at 7 inches of about 1.7 grams of fluid. Similar wicking properties were seen in a 600 g/m$^2$ basis weight, 40 weight percent absorbent material of the present invention. In contrast, the absorbent core from a Huggies® diaper, had a wicking distribution at 5 inches of less than 5 grams of fluid per gram of material. The Huggies® diaper cores did not distribute any substantial amounts of fluid beyond 5 inches.

The enhanced flexibility and wicking properties of the present absorbent material has significant advantages to a manufacturer of absorbent articles. Typically such a manufacturer purchases pulp and has to process that pulp on-line in their manufacturing plant as the final article (e.g., diaper, sanitary napkin) is being made. Such processing steps may include defibering of the pulp, adding superabsorbent and the like. In an on-line system, the rapidity with which such steps can be carried out is limited by the slowest of the various steps. An example of a pulp that requires such processing steps (e.g., defibering) is disclosed in U.S. Pat. No. 5,262,005.

The need of the manufacturer to defiberize or otherwise process existing materials on-line means that the overall production process is substantially more complex. Further, the manufacturer must purchase, maintain and operate the equipment needed to carry out such processing steps. The overall production cost is thus increased.

An absorbent material of the present invention can be directly incorporated into a desired absorbent article without the need for such processing steps. The manufacturer of the absorbent article does not have to defiber or otherwise treat the materials of the present invention in any way other than shaping the material into the desired shape. In this way, the manufacturer can speed up the assembly process and realize substantial savings in cost and time.

The material of this invention can be formed as a single blend of cellulosic fibers and SAP or air-laid as a plurality of layers or strata. In one embodiment, the material is formed as a single layer containing both cellulosic fibers and SAP. In another embodiment, the material is formed as two layers. Each of the layers can contain cellulosic fibers and SAP although it is possible to limit the SAP to only one layer. A preferred material of the present invention is air-laid as three or four lamina or strata. Those strata include a bottom layer, one or two middle layers and a top layer. Preferred embodiments of three and four layer material are set forth below. The SAP can be included in any or all of the layers. The concentration (weight percent) of SAP in each layer can vary as can the nature of the particular SAP. Five or more layer material is also contemplated by this invention.

An unexpected characteristic of the material of this invention is its ability to retain SAP when subjected to mechanical stress. In contrast to conventionally formed core materials, the material of the present invention retained over 85 percent by weight of its SAP content when subjected to 10 minutes of rigorous shaking (See, e.g., Example 4). Preferably, a material of this invention retains over 90 percent, preferably over 95 percent and, more preferably over 99 percent of its SAP under these mechanical stresses.

Even where prepared as from multiple layers, the final thickness of the formed material is low. The thickness can vary from about 0.5 mm to about 2.5 mm. In a preferred embodiment, the thickness is from about 1.0 mm to about 2.0 mm and, more preferably from about 1.25 mm to about 1.75 mm.

One embodiment of an absorbent material of the present invention is particularly well suited for use in feminine hygiene products. (See FIG. 2). Such a material has a basis weight of from about 150 $g/m^2$ to about 250 $g/m^2$ and a density between about 0.3 g/cc and 0.5 g/cc. More preferably, the density is from about 0.3 g/cc to about 0.45 g/cc and, most preferably about 0.4 g/cc.

Figure 2:
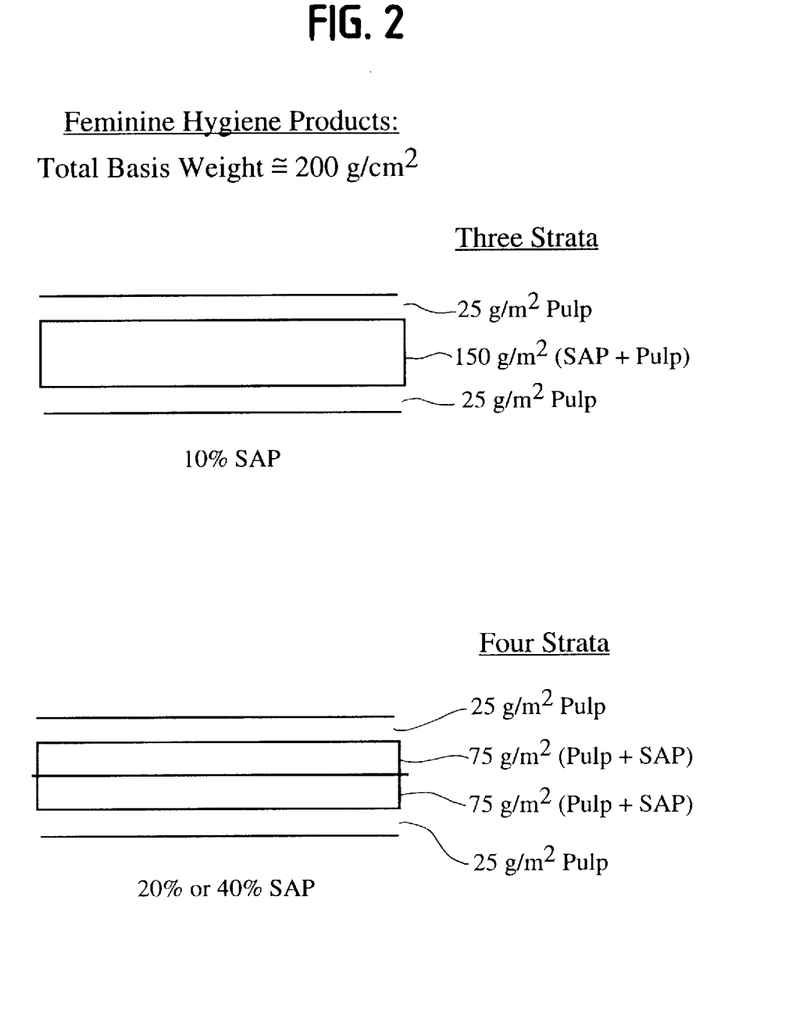
FIG. 2 shows a three and four strata embodiments of an absorbent material of the present invention for use in a diaper or incontinence device.

In one embodiment, a material for use in a feminine hygiene product is air-laid as three strata: a bottom layer of pulp (without superabsorbent) with a basis weight of about 25 $g/m^2$; a middle layer with a basis weight of about 150 $g/m^2$ and which contains from about 10 to about 30 $g/m^2$ superabsorbent and from about 120 $g/m^2$ to about 140 $g/m^2$ pulp; and a top layer of pulp (without superabsorbent) with a basis weight of about 25 $g/m^2$. Relative to the total basis weight of the material, the level of superabsorbent ranges from about 5 to about 15 weight percent ($g/m^2$ of superabsorbent per $g/m^2$ material). Preferably, the level of superabsorbent is from about 7.5 weight percent to about 12.5 weight percent of the material. Most preferably, the material contains about 10 weight percent of superabsorbent. Thus, the middle layer of the material preferably contains from about 15 $g/m^2$ to about 25 $g/m^2$ superabsorbent and from about 125 $g/m^2$ to about 135 $g/m^2$ pulp and, more preferably about 20 $g/m^2$ superabsorbent and about 130 $g/m^2$ pulp. The middle layer containing pulp and superabsorbent can be laid down as a homogeneous blend or as a heterogeneous blend wherein the level of superabsorbent varies with proximity to the bottom layer.

In another embodiment, the material is air-laid as four strata. In this embodiment, the middle layer referred to above is replaced with two middle layers: a first middle layer adjacent the top layer and a second middle layer adjacent the bottom layer. Each of the first and second middle layers independently comprises from about 10 to about 30 $g/m^2$ superabsorbent and from about 40 $g/m^2$ to about 65 $g/m^2$ pulp. When it is desired to keep absorbed fluid away from the top of the feminine hygiene product (i.e., away from the surface of the article in closest proximity to the wearer) the amount of superabsorbent in the first and second middle layers is adjusted such that there is a higher level of superabsorbent in the second middle layer. The superabsorbent in the first and second middle layers can be the same or a different superabsorbent.

Figure 3:
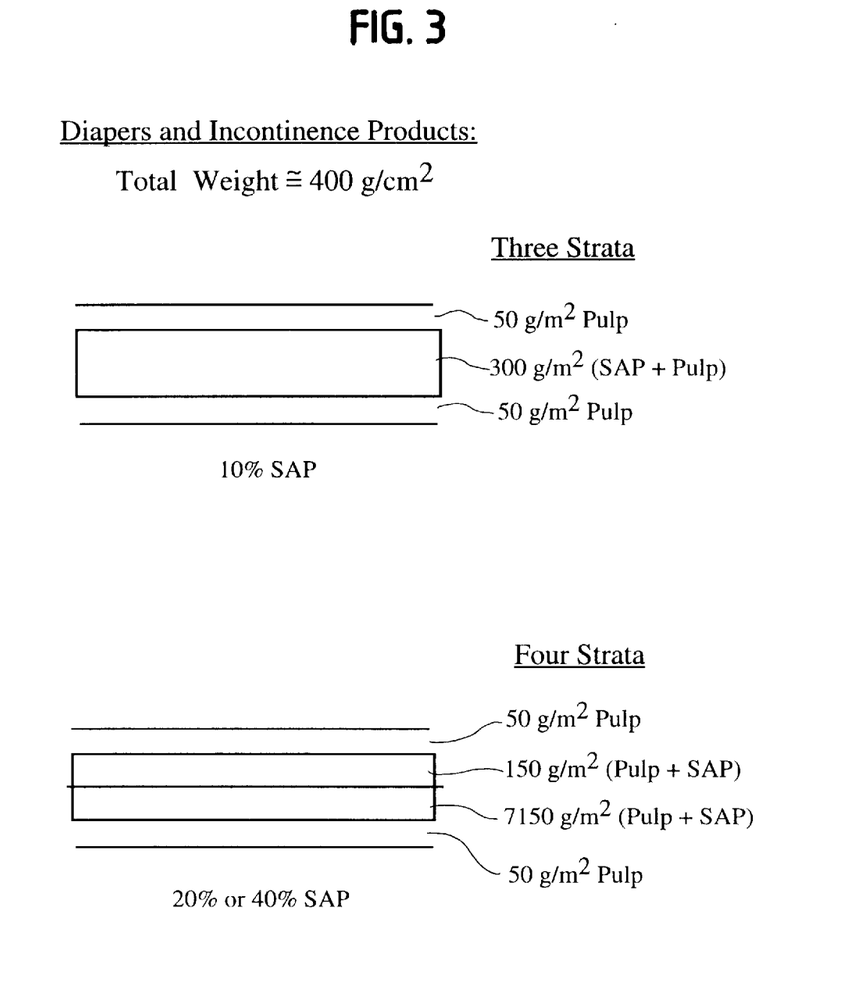
FIG. 3 shows three and four strata embodiments of an absorbent material of the present invention for use as an absorbent core in a feminine hygiene product.

Another embodiment of an absorbent material of the present invention is particularly well suited for use in diapers and incontinence products (FIG. 3). Because such articles are expected to absorb and retain larger quantities of less viscous fluid than a feminine hygiene article, such a material is heavier and, thus, has a preferred basis weight of from about 350 $g/m^2$ to about 450 $g/m^2$. The density of that material is between about 0.3 and 0.5 g/cc. More preferably, the density is from about 0.3 g/cc to about 0.45 g/cc and, most preferably about 0.4 g/cc.

In a manner similar to that described above, a material suitable for use in diapers can be air-laid as three or four strata. When three strata are used, a bottom layer has a basis weight of about 50 $g/m^2$; a middle layer has a basis weight of about 300 $g/m^2$ and contains from about 40 to about 200 $g/m^2$ superabsorbent and from about 100 $g/m^2$ to about 260 $g/m^2$ pulp; and a top layer has a basis weight of about 50 $g/m^2$. Preferably, the middle layer contains from about 70 $g/m^2$ to about 170 $g/m^2$ superabsorbent and from about 130 $g/m^2$ to about 230 $g/m^2$ pulp. Even more preferably, the middle layer contains about 80 $g/m^2$ superabsorbent and about 220 $g/m^2$ pulp or about 160 $g/m^2$ superabsorbent and about 140 $g/m^2$ pulp. The middle layer containing pulp and superabsorbent can be laid down as a homogeneous blend or as a heterogeneous blend wherein the level of superabsorbent varies with proximity to the bottom layer.

In a four strata embodiment, the middle layer is replaced with a first and second middle layer oriented as set forth above. Each of the first and second middle layers independently contains from about 20 $g/m^2$ to about 100 $g/m^2$ superabsorbent and from about 50 $g/m^2$ to about 130 $g/m^2$ pulp. In a preferred embodiment, the second middle layer has a higher level of superabsorbent than the first middle layer. In this way, the formed absorbent material has a tendency to keep absorbed fluid away from the body surface of the wearer of the article. The superabsorbent in the first and second middle layers can be the same or different.

As set forth above, a preferred cellulosic fiber for use in the present material is wood pulp. There are certain characteristics of wood pulp that make it particularly suitable for use. Cellulose in most wood pulps has a crystalline form known as Cellulose I which can be converted to a form known as Cellulose II. In the present material, wood pulp with a substantial portion of the cellulose as Cellulose II is preferred. Similarly, pulps having an increased fiber curl value are preferred. Finally, pulps having reduced levels of hemicellulose are preferred. Means for treating pulps so as to optimize these characteristics are well known in the art. By way of example, treating wood pulp with liquid ammonia is known to convert cellulose to the Cellulose II structure and to increase the fiber curl value. Flash drying is known to increase the fiber curl value of pulp. Cold caustic treatment of pulp decreases hemicellulose content, increases fiber curl and converts cellulose to the Cellulose II form. Thus it is preferred that the cellulosic fibers used to produce the material of this invention contain at least a portion of cold caustic treated pulp.

A description of the cold caustic extraction process can be found in U.S. patent application Ser. No. 08/370,571, filed on Jan. 18, 1995, pending which application is a continuation-in-part application of U.S. patent application Ser. No. 08/184,377, now abandoned filed on Jan. 21, 1994. The disclosures of both of these applications are incorporated in their entirety herein by reference.

Briefly, a caustic treatment is typically carried out at a temperature less than about 60° C., but preferably at a temperature less than 50° C., and more preferably at a temperature between about 10° C. to 40° C. A preferred alkali metal salt solution is a sodium hydroxide solution newly made up or as a solution by-product in a pulp or paper mill operation, e.g., hemicaustic white liquor, oxidized white liquor and the like. Other alkali metals such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

The following Examples illustrate preferred embodiments of the present invention and are not limiting of the specification and claims in any way.

EXAMPLE 1

A 400 g/m$^2$ absorbent material was produced in accordance with the above procedure using cold caustic extracted pulp. Overall composition of the web was 60% pulp and 40% Stockhausen T5318 SAP. The Gurley stiffness values of the absorbent material as well as absorbent cores from commercially available diapers were measured using a Gurley Stiffness Tester (Model No. 4171E), manufactured by Gurley Precision Instruments of Troy, N.Y. The instrument measures the externally applied moment required to produce a given deflection of a test strip of specific dimensions fixed at one end and having a concentrated load applied to the other end. Those commercial core materials were densified to achieve a range of densities comparable to the material of the present invention. The results are obtained in "Gurley Stiffness" values in units of milligrams. It should be noted that the higher the stiffness of the material, the less flexible and hence the less soft it is. Table 1 presents results of test.

TABLE 1

Effect of Density On Gurley Stiffness

| | | | | | |
|---|---|---|---|---|---|
| Absorbent Mat'l. | Stiffness (mg) | — | 1021 | 1175 | 1575 |
| | Density (g/cc) | — | 0.34 | 0.43 | 0.5 |
| | Ratio (stiffn/den) | | 3303 | 2732 | 3150 |
| Huggies ® Ultratrim Med. Diaper | Stiffness (mg) | 1006 | 1313 | 2450 | 3775 |
| | Density (g/cc) | .027 | 0.31 | 0.4 | 0.51 |
| | Ratio (stiffn/den) | 3726 | 4235 | 6125 | 7401 |
| Pampers ® Baby Dry Stretch Med. Diaper | Stiffness (mg) | 1188 | 1638 | 2350 | 4400 |
| | Density (g/cc) | 0.267 | 0.3 | 0.42 | 0.51 |
| | Ratio (stiffn/den) | 4449 | 5460 | 5595 | 8607 |

EXAMPLE 2

Figure 4:
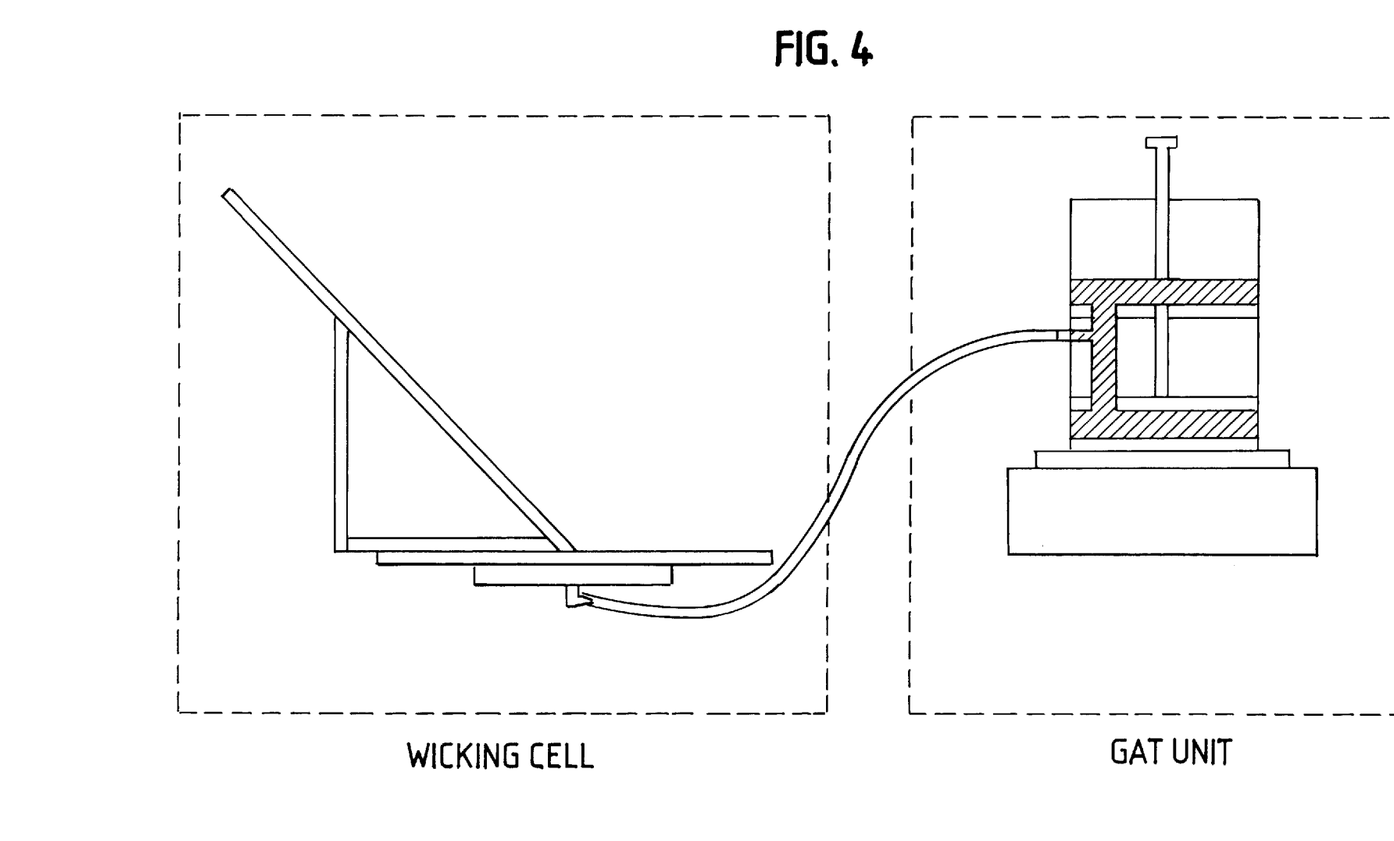
FIG. 4 is a schematic illustration of a device for measuring the wicking properties of absorbent material.

Absorbent materials of the present invention were made with basis weights of 400 g/m$^2$ and 600 g/m$^2$ containing 20 and 40 weight percent SAP, respectively. Wicking properties of the material and a core from a Huggies® diaper were measured using GATS system manufactured by M/K Systems of Danvers, Mass. FIG. 4 illustrates set up of the test. A 45° wicking test cell is attached to the absorption measurement device. The test cell essentially consists of a circular fluid supply unit for the test sample and 45° ramps. The fluid supply unit has a rectangular trough and liquid level is maintained at the constant height by the measuring unit. The test sample having dimension of 1"×12" was prepared. The sample was marked every inch along the length of the sample. The sample was then placed on the ramp of the test cell ensuring that one of the edges of the sample dips into the trough. The test was conducted for thirty minutes. Sample was removed after the specified period and cut along the marked distances. The cut pieces were placed into preweighed aluminum weighing dishes. The weighing dish containing wet samples were weighed again and then oven dried to a constant weight. By conducting a proper mass balance on the data, absorbency of the sample was determined at every inch. The following Table 2 presents results of the test:

TABLE 2

| | Absorbency (g/g) | | |
|---|---|---|---|
| Wicked Distance (in) | 400/20 Mat'l. | 600/40 Mat'l. | Huggies ® Diaper Core |
| 2 | 19.4 | 18.9 | 19.4 |
| 3 | 16.6 | 17.2 | 16.3 |
| 4 | 15.3 | 15 | 12.4 |
| 5 | 12.2 | 11.9 | 4.9 |
| 6 | 7.7 | 7.9 | 0.3 |
| 7 | 1.7 | 1.0 | |
| 8 | 0.2 | | |

The data show that the absorbent web made by the invention has a capability of transporting large amounts of fluid very rapidly from the liquid source.

EXAMPLE 3

A series of samples was evaluated for the integrity of the absorbent core in a range of material density from about 0.20 g/cc to about 0.50 g/cc. The test is performed on an Instron Universal Testing Machine. Essentially, the test measures the load required to pierce through the test sample, as described in the PFI Method of 1981. A test sample having dimensions of 50×50 mm is clamped on the Instron with a suitable fastening device. A 20 mm diameter piston traveling at the rate of 50 mm/min punctures the stationary sample. The force required to puncture the sample is measured. The following Table 3 presents results of the test.

TABLE 3

Density vs. Core Integrity

| Absorbent Mat'l. | Pad Integrity (N) | — | 12.4 | 16.3 | 15.8 |
| | Density (g/cc) | 0.20 | 0.234 | 0.326 | 0.433 |
| | Ratio (inte/den) | — | 53 | 50 | 36.5 |
| Huggies ® Ultra-trim Med. Diaper | Pad Integrity (N) | 4.1 | 5.11 | 7.6 | 8.24 |
| | Density (g/cc) | 0.19 | 0.254 | 0.328 | 0.455 |
| | Ratio (inte/den) | 21.6 | 20.4 | 23.0 | 18.2 |
| Pampers ® Baby Dry Stretch Diaper | Pad Integrity (N) | 2.9 | 3.9 | 6.6 | 9.37 |
| | Density (g/cc) | 0.16 | 0.26 | 0.38 | 0.42 |
| | Ratio (inte/den) | 18.1 | 15.0 | 17.4 | 22.3 |

The above data clearly indicate the absorbent material produced by the above invention is stronger than the conventional absorbent cores in the commercial diapers.

EXAMPLE 4

An amount of loosely held SAP in various absorbent materials was determined by shaking the material in a Ro-Tap Sieve Shaker manufactured by W. S. Tyler Co., Cleveland Ohio. Absorbent cores from commercial diapers, Huggies® Ultratrim and Pampers® Baby-dry Stretch, containing approximately 40% by weight of SAP granules were carefully removed and placed in a 28-mesh (Tyler series) sieve. Additional sieves of 35-mesh and 150-mesh were attached to the first sieve forming a column of increasingly fine sieves. The column of sieves was capped on either end to prevent the loss of fiber and/or SAP. The sieve column was placed in the shaker and agitated for 10 minutes. The amount of SAP granules shaken loose from the absorbent cores, "free SAP", was determined by combining the residue contained in each of the sieves and separating the cellulosic fiber from the SAP. Comparative data for a present absorbent material containing 40% SAP were obtained in a similar fashion. The material was formed as in Example 1.

Data in Table 4 show that the present absorbent materials retained 100% of the SAP granules while the commercial cores from the Huggies® and Pampers® products lost approximately 16.6% and 29.5% by weight of the total SAP contained in the core.

TABLE 4

Determination of Free SAP in Absorbent Cores

| Product | Total Core Weight | Approximate SAP Weight | Free SAP | Approximate % Free SAP |
|---|---|---|---|---|
| Huggies ® Ultratrims | 22.63 g | 9.05 g | 1.51 g | 16.6 |
| Pampers ® Baby-dry Stretch | 20.10 g | 8.04 g | 2.37 g | 29.5 |
| Absorbent Mat'l. | 20.45 g | 8.18 g | 0.00 g | 0.0 |

EXAMPLE 5

Absorbent material produced as in Example 1 was calendered with smooth and engraved (patterned) rolls to achieve desired density. Absorption capacity of the material against various applied pressures was measured by placing a known weight on top of the absorbent material, the known weight representing a specific pressure against the absorbent material, then contacting the absorbent material with a standard (0.9%) saline solution and allowing the material to absorb fluid until an equilibrium condition is attained. The following Table 5 presents results of the test:

TABLE 5

Effect Of Embossing On Absorbent Capacity

| Calender Type | Basis Weight Density | | Absorption Against Load (g/m$^2$) | |
| | g/m$^2$ | g/cm$^3$ | 0.3 psi | 0.7 psi |
|---|---|---|---|---|
| Engraved | 352 | 0.36 | 5430 | 4394 |
| Smooth | 405 | 0.35 | 5871 | 4666 |
| Engraved | 546 | 0.34 | 7912 | 6364 |
| Smooth | 596 | 0.35 | 8169 | 6518 |

It is evident from the test data that absorbency of calendered material with the pattern rolls is lower than the material calendered by the smooth rolls. The pattern roll essentially embosses the material. The lower absorbency may be due to damage caused to the SAP particles or to the introduction of very highly densified areas into the material as a result of the embossing. Damage to SAP granules and creation of super-densified zones in the absorbent material can have a negative impact on absorbent capacity. Therefore, it is preferred to calender the material with a smooth roll.

What is claimed is:

1. An absorbent material having a basis weight of from about 200 g/m$^2$ to about 400 g/m$^2$ which has been air-laid as a bottom layer of pulp, a middle layer of pulp and superabsorbent polymer disposed in amongst the pulp, and a top layer containing at least some pulp with said layers having been compacted together at an elevated temperature between a pair of rolls to establish a density of from about 0.35 g/cc to about 0.40 g/cc and a ratio of Gurley stiffness (mg) to density (g/cc) of less than about 3700.

2. The material of claim 1 comprising from about 10 weight percent to about 40 weight percent superabsorbent polymer.

3. The material of claim 2 having a basis weight of about 200 g/m$^2$ and comprising about 10 weight percent superabsorbent polymer.

4. The material of claim 2 having a basis weight of about 400 g/m$^2$ and comprising about 10 weight percent superabsorbent polymer.

5. The material of claim 1 wherein the middle layer comprises a first middle layer adjacent the bottom layer and a second middle layer adjacent the top layer.

6. The material of claim 5 having a basis weight of about 200 g/m$^2$ and comprising from about 20 weight percent to about 40 weight percent superabsorbent polymer.

7. The material of claim 5 having a basis weight of about 400 g/m$^2$ and comprising from about 20 weight percent to about 40 weight percent superabsorbent polymer.

8. The material of claim 1 wherein the ratio of Gurley stiffness to density is less than about 3250.

9. The material of claim 1 wherein the ratio of Gurley stiffness to density is less than about 3000.

10. The material of claim 1 having a ratio of pad integrity (newtons) to density (g/cc) of greater than about 25.0 newtons-g/cc.

11. The material of claim 1 having a ratio of pad integrity (newtons) to density (g/cc) of greater than about 30.0 newtons-g/cc.

12. The material of claim 1 having a ratio of pad integrity (newtons) to density (g/cc) of greater than about 35.0 newtons-g/cc.

13. The absorbent material in accordance with claim 1 in which said temperature is elevated at least to about 100° C.

14. An absorbent material having a top surface and a bottom surface and comprising:
(a) from about 40 weight percent to about 90 weight percent cellulosic fibers; and
(b) from about 10 weight percent to about 60 weight percent superabsorbent polymer, the material having been compacted at an elevated temperature between a pair of rolls to establish a water content of less than about 10 weight percent, a density of greater than about 0.25 g/cc, a ratio of Gurley stiffness (mg) to density (g/cc) of less than about 3700 and a pad integrity of greater than about 12 newtons, the top surface of said absorbent material being substantially free of superabsorbent polymer.

15. The material of claim 14 containing from about 50 to about 90 weight percent cellulosic fibers.

16. The material of claim 14 containing from about 60 to about 80 weight percent cellulosic fibers.

17. The material of claim 14 containing from about 10 to about 50 weight percent superabsorbent polymer.

18. The material of claim 14 containing from about 20 to about 40 weight percent superabsorbent polymer.

19. The material of claim 14 having a density of from about 0.30 to about 0.50 g/cc.

20. The material of claim 14 having a density of from about 0.30 to about 0.45 g/cc.

21. The material of claim 14 having a density of from about 0.30 to about 0.40 g/cc.

22. The material of claim 14 having a ratio of Gurley stiffness to density of less than about 3250.

23. The material of claim 14 having a ratio of Gurley stiffness to density of less than about 3000.

24. The material of claim 14 having a ratio of pad integrity to density of greater than about 25.0.

25. The material of claim 14 having a ratio of pad integrity to density of greater than about 30.0.

26. The material of claim 14 having a ratio of pad integrity to density of greater than about 35.0.

27. The material of claim 14 having a basis weight of from about 50 g/m$^2$ to about 700 g/m$^2$.

28. The material of claim 14 having a basis weight of from about 100 g/m$^2$ to about 600 g/m$^2$.

29. The material of claim 14 having a basis weight of from about 200 g/m$^2$ to about 400 g/m$^2$.

30. The material of claim 14 that is air-laid as a plurality of layers.

31. The material of claim 30 that is air-laid as 3, 4 or 5 layers.

32. The material of claim 30 wherein at least one layer comprises pulp without superabsorbent polymer.

33. The material of claim 14 that has a 45° wicking distribution at 5 inches of at least 5 grams of saline per gram of material.

34. The material of claim 14 that has a 45° wicking distribution at 5 inches of at least 9 grams of saline per gram of material.

35. The material of claim 14 that has a 45° wicking distribution at 5 inches of at least 11 grams of saline per gram of material.

36. The material of claim 14 that has a thickness of from about 0.5 mm to about 2.5 mm.

37. The material of claim 14 that has a thickness of from about 1.0 mm to about 2.0 mm.

38. The material of claim 14 that has a thickness of from about 1.25 mm to about 1.75 mm.

39. The material of claim 14 further comprising from about 1 weight percent to about 20 weight percent synthetic fibers.

40. The material of claim 14 that retains more than about 90 weight percent of superabsorbent polymer after shaking for 10 minutes in a Ro-Tap Sieve Shaker.

41. The material of claim 14 that retains more than about 95 weight percent of superabsorbent polymer after shaking for 10 minutes in a Ro-Tap Sieve Shaker.

42. The absorbent material in accordance with claim 14 in which said temperature is elevated at least to about 100° C.

43. An absorbent material having a top surface and a bottom surface and comprising:
(a) from about 40 weight percent to about 90 weight percent cellulosic fibers; and
(b) from about 10 weight percent to about 60 weight percent superabsorbent polymer, the material having been compacted at an elevated temperature between a pair of rolls to establish a water content of less than about 10 weight percent, a density of greater than about 0.25 g/cc, a ratio of Gurley stiffness (mg) to density (g/cc) of less than about 3700, a ratio of pad integrity (newtons) to density (g/cc) of greater than about 25.0 newtons-g/cc, and 45° wicking distribution at 5 inches of at least 5 grams of saline per gram of material, the top surface of said absorbent material being substantially free of superabsorbent polymer.

44. The absorbent material in accordance with claim 43 in which said temperature is elevated at least to about 100° C.

45. An absorbent material having a basis weight of from about 200 g/m$^2$ to about 400 g/m$^2$, a density of from about 0.35 g/cc to about 0.40 g/cc and a ratio of Gurley stiffness (mg) to density (g/cc) of less than about 3700, wherein the material is air-laid as a bottom layer of pulp, a middle layer of pulp and superabsorbent polymer disposed in amongst the pulp, and a top layer of pulp wherein cellulosic fibers comprise said pulp produced by a process that includes the step of treating a liquid suspension of pulp at a temperature of 15° C. to about 60° C. with an aqueous alkali metal salt solution having an alkali metal salt concentration of from about 2 weight percent to about 25 weight percent of said solution for a period of time ranging from about 5 minutes to about 60 minutes.

46. An absorbent material comprising:
(a) from about 40 weight percent to about 90 weight percent cellulosic fibers; and
(b) from about 10 weight percent to about 60 weight percent superabsorbent polymer, the material having a water content of less than about 10 weight percent, a density of greater than about 0.25 g/cc, a ratio of Gurley stiffness (mg) to density (g/cc) of less than about 3700, and a pad integrity of greater than about 12 newtons wherein the cellulosic fibers comprise pulp produced by a process that includes the step of treating a liquid suspension of pulp at a temperature of from 15° C. to about 60° C. with an aqueous alkali metal salt solution having an alkali metal salt concentration of from about 2 weight percent to about 25 weight percent of said solution for a period of time ranging from about 5 minutes to about 60 minutes.

47. An absorbent material comprising:
(a) from about 40 weight percent to about 90 weight percent cellulosic fibers; and
(b) from about 10 weight percent to about 60 weight percent superabsorbent polymer, the material having a water content of less than about 10 weight percent, a density of greater than about 0.25 g/cc, a ratio of Gurley stiffness (mg) to density (g/cc) of less than about 3700, a ratio of pad integrity to density of greater than about 25.0 newtons-g/cc, and 45° wicking distribution at 5 inches of at least 5 grams of saline per gram of material wherein the cellulosic fibers comprise pulp produced by a process that includes the step of treating a liquid suspension of pulp at a temperature of from 15° C. to about 60° C. with an aqueous alkali metal salt solution having an alkali metal salt concentration of from about 2 weight percent to about 25 weight percent of said solution for a period of time ranging from about 5 minutes to about 60 minutes.

48. An absorbent material having a top surface and a bottom surface and comprising:
   (a) from about 40 weight percent to about 90 weight percent cellulosic fibers; and
   (b) from about 10 weight percent to about 60 weight percent superabsorbent polymer, the material having been compacted at an elevated temperature between a pair of rolls to establish a water content of less than about 10 weight percent, a density of greater than about 0.25 g/cc and a ratio of Gurley stiffness (mg) to density (g/cc) of less than about 3700; and the capability of the material to retain more than about 85 weight percent of superabsorbent polymer after shaking for 10 minutes in a Ro-Tap Sieve Shaker, the top surface of said absorbent material being substantially free of superabsorbent polymer.

49. The absorbent material in accordance with claim 48 in which said temperature is elevated at least to about 100° C.

50. An absorbent material having a top surface and a bottom surface and comprising:
   cellulosic fibers and superabsorbent polymer disposed amongst at least some of said cellulosic fibers, the material having been compacted at a temperature of at least about 100° C. to establish a water content of less than about 10 weight percent, a density of greater than about 0.25 g/cc, a ratio of Gurley stiffness (mg) to density (g/cc) of less than about 3700, and a pad integrity of greater than about 12 newtons, the top surface of said absorbent material being substantially free of superabsorbent polymer.

* * * * *